United States Patent [19]

Kirsch

[11] Plant 5,189

[45] Feb. 14, 1984

[54] LILY NAMED LE REVE

[75] Inventor: Ted T. Kirsch, Myrtle Point, Oreg.

[73] Assignee: Sun Valley Bulb Farms, Inc., Myrtle Point, Oreg.

[21] Appl. No.: 406,379

[22] Filed: Aug. 9, 1982

[51] Int. Cl.[3] ..... A01H 5/00
[52] U.S. Cl. ..... Plt./68
[58] Field of Search ..... Plt./68

*Primary Examiner*—Robert E. Bagwill
*Attorney, Agent, or Firm*—Chas. W. Rummler

[57] ABSTRACT

A new and distinct lily cultivar of the Parkmanni type of Oriental hybrid particularly distinguished by its light pink, outward and slightly upfacing bowl-shaped flowers which are borne in a raceme arrangement on long strong stems and still upward projecting pedicels growing off the main stem, usually with one bud or flower on each pedicel. The fewer the flowers on the stem, the more upright the pedicels and buds become. In addition, it has green, glossy and relatively disease resistant foliage.

2 Drawing Figures

BACKGROUND OF THE NEW PLANT

My new variety of lily plant originated as a seedling of unknown parentage discovered by me at my nursery in Arcata, Calif. Its delicately pastel colored flowers, and its rich green foliage prompted me to asexually propagate this new plant for study with the result that I have found additional advantageous and distinctive characteristics in the new plant which makes it a valuable addition to the commercial field of lily culture for cut flower production. Propagation of this new lily through successive generations by means of scales and tissue culture at Arcata has shown that it is relatively disease resistant and that its distinctive characteristics hold true from generation to generation and appear to be firmly fixed.

DESCRIPTION OF THE DRAWING

This new variety of lily plant is illustrated by the accompanying photographic drawing which has 2 views in full color, showing a full grown blooming plant in one view and a close-up view of several blooms in the other view. The color rendition is as nearly true as can reasonably be obtained by conventional photographic procedures.

DESCRIPTION OF THE NEW PLANT

The following is a detailed description of my new lily plant cultivar as observed at Arcata, Calif., with color designations according to the R.H.S. Colour Chart published by The Royal Horticultural Society of London, England, the observations being made on greenhouse grown plants at Arcata, Calif. in the spring of 1981.

THE PLANT

Origin: Seedling.
Parentage: Unknown.
Classification:
*Oriental hybrid.*—Parkmanni.
Form: Tall single stem from each bulb.
Height: 2–3 feet at maturity.
Growth: Sturdy and upright with excellent strength.
Cane size: Stems grow from ¼-inch in diameter from small bulbs to ½-inch from larger bulbs.

Leaves:
*At flower cluster.*—Two in number, one at the base of each pedicel — 4 inches long and 1 inch wide — and one on the pedicel approximately 1 inch from the flower — 3 inches long and ½-inch wide.
*Shape.*—Lanceolate.
*Texture.*—Leathery.
*Aspect.*—Smooth.
*Ribs and veins.*—Distinct longitudinal veins from base to tip.

Bulblets:
*Underground stem.*—Occurrence — one to two on each healthy normal plant at digging time.
*Size.*—From ¼-inch to ½-inch in diameter.
*Color.*—White, with occasional pink shading at the tips.

Bulbs:
*Size.*—From about 4 inches to 12 inches in circumference, depending on age.
*Color.*—White, with yellow and pink overtones. As bulbs become larger and older, the overtones of yellow and pink become more and more prominent.

THE BUD

Form: Elliptic with acute apex.
Size: Average 3½ to 4 inches long, and 1½ to 1¾ inches in diameter. Could be classified as a comparatively "fat" bud.
Number: Usually one on each pedicel, with 1 to 8 buds on a plant according to culture and bulb size.
Opening: Normal buds open successively from the lowermost bud to the top bud which is the last to open.
Color: Whitish-pink at the tip, deepening to a darker pink at the base, midribs are light green, when sepals first divide and petals begin to unfurl.
Surface: Rugose (wrinkled), leathery, with prominent veins.
Pedicel: Strong and generally upright and glabrous; green underneath and green with maroon splotches on top. Angles about 45° from vertical on medium sized bulbs.
*Length.*—3 to 4 inches.

THE FLOWER

Blooming habit: Annually. Blooming profusely in late July outside under normal lily forcing conditions and temperatures. In a greenhouse, it blooms in 95 to 105 days.

Size of flower:

*Medium.*—5 to 6 inches in diameter.

Borne:

*From larger bulbs.*—The inflorescence has a raceme arrangement with each pedicel bearing one bud. The size of the bulb and its cultural care will determine the number of buds to be found on any given inflorescence. From large bulbs this lily may have 3 to 6 blooms open at one time.

Shape: Bowl, with uniformly spaced petals in star arrangement with tips of petals curving back slightly.

Petalage: Petals normal, three sepals and three petals.

*Form.*—Oval, with obtuse apex and a center furrow bisecting each petal longitudinally. Edges slightly undulate.

*Color.*—(When greenhouse grown on the West Coast.) Upper side — Upon opening the petal is RHS Red Purple 63D. The inside half of the petals on either side of the midrib is moderately spotted with small, inconspicuous oblong maroon spots. Under side — RHS Red Purple 68D, the midrib slightly lighter and the base of the sepals slightly darker; glabrous.

*Texture.*—Leathery.

*Aspect.*—Velvety.

*Papillae.*—Present on the petals from 10 to 20 in number.

Fragrance: Sweet.

Discoloration: The color fades ever so slightly as blossom matures.

Effect of weather: Flower generally not affected by wet weather, but flower ages as temperature rises.

Persistence: The flower tends to hang on and dry.

Lasting quality.

*On the plant.*—2 to 3 weeks, depending on the size of the bulb and its environmental temperature.

*As a cut flower.*—10 to 14 days.

REPRODUCTIVE ORGANS

Stamens:

*Number.*—6, orderly around pistil.

*Anthers.*—Length — $\frac{5}{8}$ inches, deep rust color.

*Filaments.*—3 inches long, yellow-green color.

Pistils:

*Number.*—One.

*Style.*—Dark green color about $2\frac{1}{2}$ inches long.

*Stigma.*—Purple grey.

Ovary: Classified as a schizocarp, about $1\frac{1}{2}$ inches long swelling in diameter as it matures, dehiscing into thirds and containing 6 rows of seeds of the usual shape for lilies.

I claim:

1. A new and distinct variety of Oriental hybrid lily plant substantially as herein shown and described, characterized by its profuse production of pink, somewhat upfacing bowl-shaped flowers borne on strong stiff upward-projecting pedicels, and the long lasting quality of the blooms whether on the plant or as cut flowers.

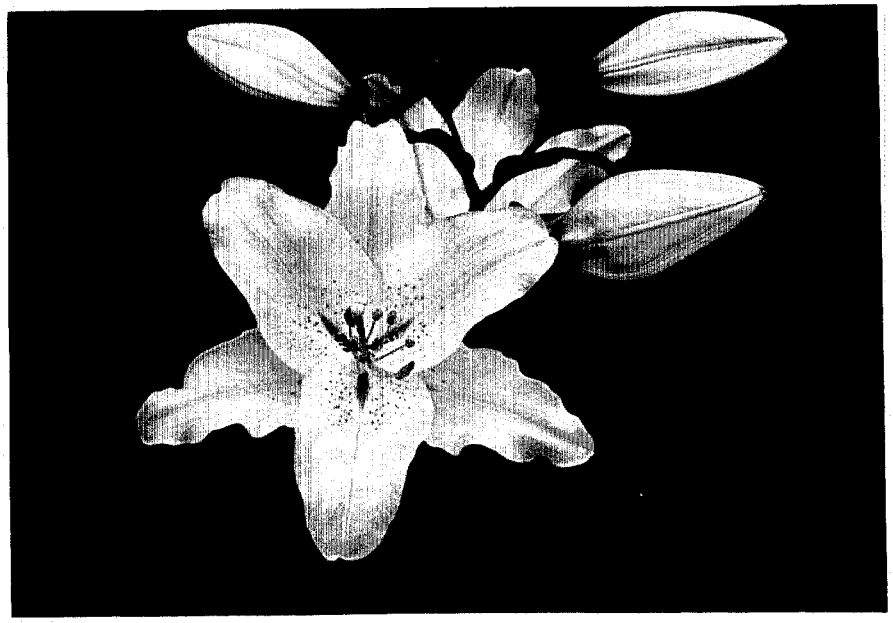
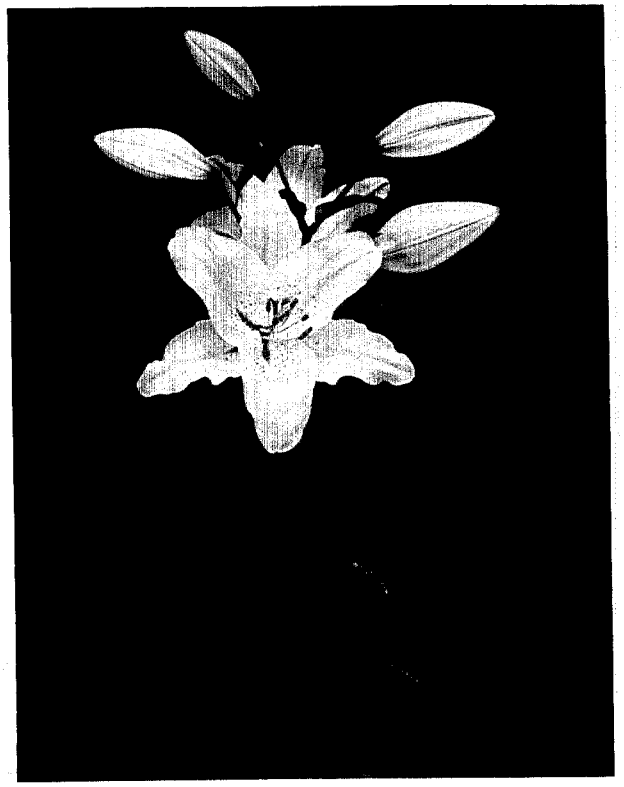

* * * * *